United States Patent [19]

Ross et al.

[11] Patent Number: 4,649,145
[45] Date of Patent: Mar. 10, 1987

[54] THIAZOLE DERIVATIVES

[75] Inventors: Barry C. Ross, Luton; Jeffrey D. Michael, Milton Keynes, both of Great Britain

[73] Assignee: Hoechst UK Limited, Great Britain

[21] Appl. No.: 803,523

[22] Filed: Dec. 2, 1985

Related U.S. Application Data

[63] Continuation of Ser. No. 524,242, Aug. 18, 1983, abandoned.

[30] Foreign Application Priority Data

Aug. 20, 1982 [GB] United Kingdom ................ 8224024

[51] Int. Cl.[4] ................ C07D 417/12; A61K 31/425
[52] U.S. Cl. .................................... 514/370; 548/194
[58] Field of Search ........................ 548/194; 514/370

[56] References Cited

U.S. PATENT DOCUMENTS 4,374,836  2/1983  Yellin .................. 424/251

FOREIGN PATENT DOCUMENTS 10894    5/1980  European Pat. Off. ............ 548/194
14057    8/1980  European Pat. Off. ............ 548/194
0028117  5/1981  European Pat. Off. ............ 514/370
30092    6/1981  European Pat. Off. ............ 548/194
1419994  1/1976  United Kingdom ................ 514/370
2001624  2/1979  United Kingdom ................ 548/194

Primary Examiner—Robert Gerstl
Attorney, Agent, or Firm—Finnegan, Henderson, Farabow, Garrett & Dunner

[57] ABSTRACT

New thiazole derivatives of the general formula I

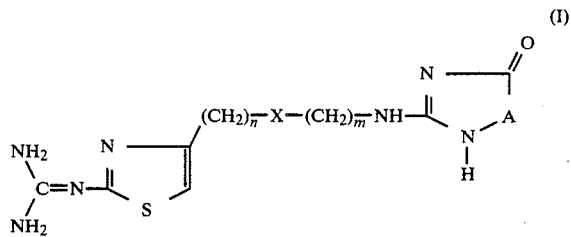

and their salts with physiologically acceptable acids are described as well as a process for their manufacture. The new compounds exhibit histamine H-2 antagonist activity and may thus be used to inhibit gastric acid secretion and to treat gastric and peptic ulcers.

7 Claims, No Drawings

THIAZOLE DERIVATIVES

This application is a continuation of application Ser. No. 524,242, filed Aug. 18, 1983, now abandoned.

The present invention relates to thiazole derivatives which have histamine H-2 antagonist activity. The invention also relates to processes for the preparation of these derivatives, to pharmaceutical preparations comprising them, and to their use.

Histamine is one of a number of naturally occurring physiologically active substances which are thought to interact with specific receptors. In the case of histamine, there are at least two types: one is called H-1 receptor (Ash and Schild, Brit. J. Pharmac. 1966, 27, 427), and the other is called the H-2 receptor (Black et al, Nature 1972, 236, 385). The action of histamine at the H-1 receptors, for example, stimulation of bronchial and gastro-intestinal smooth muscle, is blocked by the compounds generally known as "antihistamines", but which are now also called histamine H-1 antagonists, for example, mepyramine. The action of histamine at the H-2 receptors, for example, stimulation of gastric acid secretion and heart rate, is not blocked by mepyramine but is blocked by other compounds, for example, burimamide and cimetidine.

Histamine H-2 antagonists may be used to treat those conditions resulting from stimulation by histamine of H-2 receptors, either alone, for example, in inhibiting gastric acid secretion and thus treating its sequelae, for example, gastric and peptic ulcers; or together with H-1 antagonists for example, allergic and certain inflammatory conditions.

The present invention provides compounds of the general formula I, which are histamine H-2 antagonists:

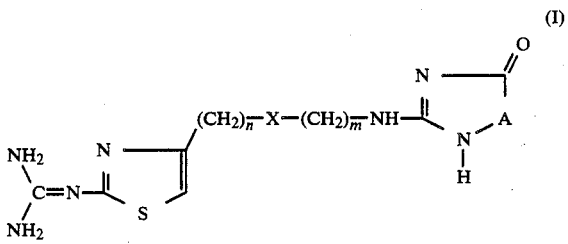

in which
X represents —O—, —CH$_2$—, —S—, or —NH—,
n represents 1 or 2,
m represents 2, 3 or 4, and
A represents

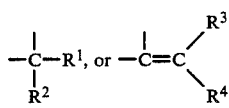

where
R$^1$ and R$^2$, which may be the same or different, each represents a hydrogen atom, an alkyl group having from 1 to 10 carbon atoms, an aryl group, an aralkyl group having from 1 to 10 carbon atoms in the alkyl moiety, or an alkenyl or alkynyl group having from 2 to 10 carbon atoms, the above groups being unsubstituted or substituted, or
R$^1$ and R$^2$ together with the carbon atom to which they are linked form a ring which may contain one or more double bonds and may contain an oxygen atom, the total number of atoms in the ring being 5 or 6, or where
R$^3$ and R$^4$, which may be the same or different, each represents a hydrogen atom; a straight or branched chain alkyl group having from 1 to 10 carbon atoms; an alkenyl group having from 2 to 10 carbon atoms; an aryl group; a five or six membered heterocycle containing one or more —N—, —S—, or —O— atoms, especially a pyridine, thiophen, furan or tetrahydrofuran group; an —COOR$^5$ group in which R$^5$ denotes a hydrogen atom or an alkyl group having from 1 to 4 carbon atoms; or a —CONH$_2$ group; or R$^3$ and R$^4$ together with the carbon atom to which they are bonded form a cyclohexyl or cyclopentyl ring.

Isomerism may occur in compounds of the general formula I. It is to be understood that all possible isomers of a compound of formula I are included, and that references to a compound of formula I include individual isomers and also mixtures of any two or more isomers.

The invention also provides salts of a compound of formula I, especially physiologically tolerable salts thereof.

In the present specification the term "lower" is used to denote a group, radical or molecule having from 1 to 4 carbon atoms. Unless stated otherwise "halogen" denotes chlorine, bromine, iodine and fluorine.

An alkyl or alkenyl group has from 1 to 10 atoms and preferably 1 to 6 carbon atoms, and may be unsubstituted or substituted, for example by one or more groups, which may be the same or different, selected from hydroxyl groups; —OR$^6$ groups in which R$^6$ represents a lower alkyl group or an aryl group; —NR$^7$R$^8$ groups in which R$^7$ and R$^8$ each denotes a hydrogen atom, a lower alkyl group, an aryl group, or a lower acyl group; —COOR$^9$ groups, in which R$^9$ represents a hydrogen atom or a lower alkyl group, —CONR$^7$R$^8$ in which R$^7$ and R$^8$ are defined above and in addition together with the N atom may form a 5 or 6 membered ring; phenyl groups which may be substituted by a lower alkyl, lower alkoxy, phenoxy, halogen, dimethylaminomethyl, trifluoromethyl, nitro, cyano, sulphonic acid or sulphonamide substituent; heterocyclic groups, for examle, pyridine, thiophen, and furan groups, which may be substituted as defined above for phenyl groups; lower alkylsulphonyl and arylsulphonyl groups; and nitrile groups. ("Acyl" is carboxylic acyl.)

An aryl group is especially a phenyl group and may carry one or more substituents as defined above for phenyl. An aralkyl group is preferably a benzyl group and the aryl moiety may be substituted as defined above for phenyl groups.

It will be appreciated by the worker in the art that substituents that are incompatible for steric reasons or because of potential inter-reactions should not be chosen. The worker will also use his normal discretion in the number of substituents chosen.

The present invention also provides a process for the production of a compound of the general formula I, which comprises (a) reacting a 2-alkylthio-4-imidazolidinone of the general formula II

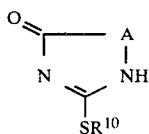

in which A is as defined above for compound I and $R^{10}$ represents an alkyl group, especially a lower alkyl group, with a 2-guanidinothiazole of the general formula III

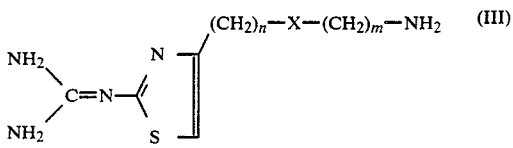

in which X, n and m are as defined above for compound I; (Compounds of the general formula III are described in UK Specification No. 2 001 624A.)

(b) reacting a 2-alkylthioimidazolidin-4-one of the general formula II with a compound of the general formula IV

in which X and m are defined as above, and reacting the resulting compound of formula V

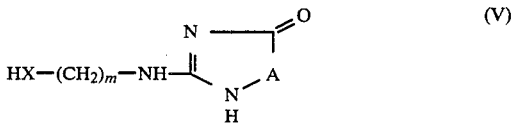

with a compound of the general formula VI

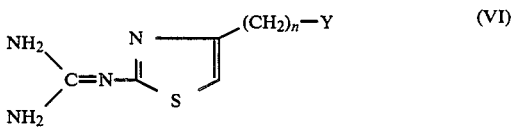

in which Y denotes a halogen atom, an alkoxy or hydroxyl group, or a sulphonic acid ester; and, if desired, carrying out any one or more of the following:

(a) converting a resulting compound of formula I into a salt thereof or (b) converting a resulting salt of a compound of formula I into the free base form, and (c) converting a substituent of $R^1$ and/or $R^2$ into another substituent thereof.

Salts of formula I are generally acid addition salts, which may be prepared in the usual manner by reaction with an acid. Examples of physiologically tolerable acid addition salts are those with hydrobromic, hydrochloric, sulphuric, maleic, fumaric, succinic or citric acid.

A compound of formula I in the form of an acid addition salt may be converted into the free base form by reaction with a base in the usual manner.

Compounds II and III are generally reacted in a solvent or diluent, preferably an alcohol, at a temperature within the range of, for example, from 0° to 100° C., generally from 60° to 80° C. The compound of formula III should be reacted in the form of the free base, as shown. If it is initially present in the form of an acid addition salt, for example, as the hydrochloride or hydrobromide, this should be converted into the free base during or, preferably, before reaction with compound II. Conversion is carried out with a base, for example, triethylamine, sodium hydroxide or potassium hydroxide.

Compound II is generally reacted with compound IV under the conditions described above for the reaction of compounds II and III. Again, compound IV should be reacted in the form of the free base. In the subsequent reaction of compounds V and VI, when Y represents a halogen atom, the reaction is generally carried out in a solvent or diluent, and generally in the presence of a base. When Y represents an alkoxy or hydroxyl group, the reaction is generally carried out in a mineral acid, preferably a concentrated mineral acid, for example, concentrated hydrochloric or hydrobromic acid.

A compound of formula II may be produced by alkylating a compound of formula VII

in which A is as defined above. The alkylation may be carried out with any alkylating agent, for example, an alkyl sulphate, for example, methyl sulphate or ethyl sulphate, methylfluorosulphonate, or an alkyl halide, especially an alkyl iodide, for example, methyl iodide, The reaction is carried out in the presence of an inorganic base, for example, sodium or potassium hydroxide, or sodium or potassium carbonate. The reaction is generally carried out in a solvent or diluent, and at a temperature of from 0° to 100° C., preferably at room temperature.

A few examples of 2-alkylthio-4-imidazolidinones have been prepared previously, see for example, H. Biltz, Chem. Berichte 42, 1792 (1909); Cook and Pollock, J. Chem. Soc. 1898 (1950); Shalaby, Z. Naturforsch. 32, 948 (1977).

A compound of formula VII in which A represents the group

where $R^1$ and $R^2$ are defined as above, may be prepared according to known methods, see for example, M. Jackman, M. Klenk, B. Fishburn, B. F. Tullar and S. Archer, J. Am. Chem. Soc. 70; 2884 (1948).

A compound of formula VII in which A represents the group

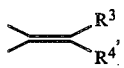

where $R^3$ and $R^4$ are defined as above, may be prepared by reacting 2-thiohydantoin or 3-acetyl-2-thiohydantoin with an aldehyde or ketone which comprises the groups $R^3$ and $R^4$ under a variety of reaction conditions, some examples of which are: sodium acetate/acetic acid—T. B. Johnson, J. Am. Chem. Soc. 61, 2485

(1939); sodium acetate/acetic anhydride—C. Niemann et al, J. Am. Chem. Soc. 64, 1678 (1942); sodium acetate alone—V. du Vigneaud, J. Biol. Chem. 159, 385 (1945); pyridine/piperidine—W. J. Boyd, Biochem. J. 29, 542 (1935); diethylamine/ethanol—A. P. Phillips, J. Am. Chem. Soc. 67, 744 (1945).

Histamine $H_2$-antagonists have been shown to inhibit gastric acid secretion in a variety of test animals and in man. These compounds are also capable of blocking the gastric secretion stimulated by exogenously administered histamine or pentagastrin; see Brimblecombe et al., J. Int. Med. Res. 3, 86 (1975).

Compounds of this invention were tested for antisecretory activity in the perfused rat stomach. The method of Ghosh and Schild, Brit. J. Pharmacol. 13, 54 (1958) as modified by Lawrence and Smith, Europ. J. Pharmacol. 25, 389 (1974) was used to prepare the test animals and acid secretion was stimulated by infusing either histamine or pentagastrin at a constant rate. After the secretion plateau was reached, the test compound was administered i.v. and the amount of compound required to inhibit the stimulated secretion by 50% was determined.

According to the test results obtained, the compounds of Formula I of this invention inhibit gastric acid secretion. Consequently, these compounds may be used to treat all pathological conditions in man and animals which are due to an overproduction of gastric acid, e.g. duodenal ulcer, gastric ulcer, gastritis, Zollinger-Ellison syndrome, reflux oesophagitis.

The $ID_{50}$ values for some of the compounds listed under example I of this invention are given in the following table.

| Compounds Tested for Inhibition of Gastric Acid Secretion in the Perfused Rat Stomach | |
|---|---|
| Compounds from Example I | $ID_{50}$ mg/kg |
| 64 | 0.45 |
| 65 | 0.70 |
| 69 | 0.15 |
| 70 | 1.5 |
| 71 | 0.2 |
| 72 | 0.16 |
| 74 | 2.5 |
| 77 | 0.5 |
| 78 | 1.0 |
| 80 | 0.5 |
| 81 | 1.2 |
| 82 | 0.6 |
| 83 | 3.5 |
| 85 | 0.2 |
| 86 | 0.02 |
| 87 | 0.10 |
| 88 | 0.10 |
| 89 | 0.15 |
| 90 | 0.18 |
| 91 | 0.18 |
| 92 | 0.07 |
| 93 | 0.07 |
| 94 | 0.06 |
| 96 | 10.0 |
| 97 | 0.5 |
| Cimetidine[1] | 2.5 |

[1]N—cyano-N'—methyl-N''—{2-[(4-methyl-5-imidazolyl)methyl-thio]ethyl}guanidine.

The present invention provides a pharmaceutical preparation which comprises a compound of the general formula I or a physiologically tolerable salt thereof, in admixture or conjunction with a pharmaceutically suitable carrier. A preparation of the invention may be in a form suitable for oral, parenteral or topical administration. The amount of a compound of formula I or of a physiologically tolerable salt thereof to be administered is, for example, in the range of from 0.01 to 10 mg/kg body weight. The present invention also provides the use of a compound of the general formula I or of a physiologically tolerable salt thereof as a histamine H-2 antagonist.

The following Examples illustrate the invention.

EXAMPLE A 5-(2-Butyl)-2-thioxo-4-imidazolidinone

A mixture of 26.2 g of dl-leucine and 15.2 g of ammonium thiocyanate in 100 ml of acetic anhydride and 10 ml of acetic acid is heated at 100° C. for 45 minutes. The resulting clear solution is cooled and poured onto 500 g of ice/water with rapid stirring. The solid product is filtered off, washed with water, and recrystallized from ethanol to yield 28.3 g (66%) of 5-(1-methylpropyl)-1-acetyl-2-thioxo-4-imidazolidinone as a white crystalline solid, m.p. 132°-3° C.

TLC: silica gel: $CHCl_3/CH_3OH$ (4:1) $R_f$=0.75.

35 g of the above product is suspended in 200 ml of 10% aqueous HCl and heated to 100° C. for 45 minutes. The resulting solution is cooled and 5-(1-methylpropyl)-2-thioxo-4-imidazolidinone crystallized out as a white solid. This is filtered off, washed with water, and dried to yield 23.2 g, m.p. 129°-30° C.

TLC: silica gel; $CHCl_3/CH_3OH$ (4:1) $R_f$=0.70.

The 2-thioxo-4-imidazolidinones 1 to 13 (Table I) are prepared by using an equivalent amount of the appropriate amino acid in place of the leucine used in the above procedure.

TABLE 1

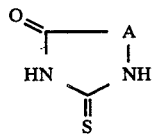

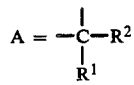

| | $R^1$ | $R^2$ | m.p. (°C.) | nmr[1] ($\delta_{TMS}$ = 0) |
|---|---|---|---|---|
| 1. | H | $CH_3$— | 165-6 | $\delta$ = 1.25 ppm (doublet, 3H) |
| | | | | $\delta$ = 4.20 ppm (quad., 1H) |

TABLE 1-continued $$\underset{S}{\overset{O}{\underset{HN}{\bigtriangleup}}}\overset{A}{\underset{NH}{\bigtriangleup}}$$

$$A = -\underset{R^1}{\overset{|}{\underset{|}{C}}}-R^2$$

| | $R^1$ | $R^2$ | m.p. (°C.) | nmr[1] ($\delta_{TMS} = 0$) | |
|---|---|---|---|---|---|
| 2. | H | $CH_3CH_2-$ | 165-6 | $\delta =$ 0.85 | (triplet, 3H) |
| | | | | 1.60 | (multiplet, 2H) |
| | | | | 4.02 | (triplet, 1H) |
| 3. | H | $CH_3(CH_2)_2-$ | 157-8 | $\delta =$ 0.60-1.80 | (multiplet, 7H) |
| | | | | 4.01 | (triplet, 1H) |
| 4. | H | $\underset{CH_3CH_2-}{\overset{CH_3}{|}}$ | 145-6 | $\delta =$ 0.83 | (doublet, 3H) |
| | | | | 0.97 | (doublet, 3H) |
| | | | | 2.00 | (multiplet, 1H) |
| | | | | 4.03 | (doublet, 1H) |
| 5. | H | $\underset{CH_3CH_2CH-}{\overset{CH_3}{|}}$ | 130-1 | $\delta =$ 0.95-2.1 | (multiplet, 3H) |
| | | | | 0.92 | (doublet, 3H) |
| | | | | 0.82 | (triplet, 3H) |
| | | | | 4.15 | (doublet, 1H) |
| 6. | H | $\underset{CH_3CHCH_2-}{\overset{CH_3}{|}}$ | 177-8 | $\delta =$ 0.90 | (doublet, 6H) |
| | | | | 1.30-2.03 | (multiplet, 3H) |
| | | | | 4.20 | (triplet, 1H) |
| 7. | H | $CH_3(CH_2)_3-$ | 135-6 | $\delta =$ 1.30 | (multiplet, 9H) |
| | | | | 4.20 | (triplet, 1H) |
| 8. | H | $CH_3(CH_2)_5-$ | 140-1 | $\delta =$ 1.30 | (multiplet, 13H) |
| | | | | 4.10 | (triplet, 1H) |
| 9. | H | $CH_3SO_2(CH_2)_2-$ | 233-6 | $\delta =$ 2.10 | (multiplet, 4H) |
| | | | | 3.0 | (singlet, 3H) |
| | | | | 4.40 | (triplet, 1H) |
| 10. | $CH_3-$ | $CH_3-$ | 163-4 | $\delta =$ 1.30 | (singlet, 6H) |
| 11. | H | $\text{C}_6\text{H}_5\text{CH}_2-$ | 181-2 | $\delta =$ 3.00 | (doublet, 2H) |
| | | | | 4.50 | (triplet, 1H) |
| | | | | 7.10 | (singlet, 5H) |
| 12.[2] | H | $NH_2CO(CH_2)_2-$ | 196-8° | $\delta =$ 1.50-2.50 | (multiplet, 4H) |
| | | | | 4.20 | (triplet, 1H) |
| 13.[3] | H | $CH_3OCO(CH_2)_2-$ | 122-4° | $\delta =$ 2.00-3.00 | (multiplet, 3H) |
| | | | | 3.73 | (singlet, 3H) |
| | | | | 4.20 | (triplet, 1H) |

Footnotes:
[1] All compounds dissolved in DMSO-$d_6$ for nmr measurement.
[2] Intermediate 1-acetate hydrolysed with $CH_3OH/KOH$ at room temperature.
[3] Prepared by treating the amide (12) with $CH_3OH/HCl$.

EXAMPLE B

5-Benzylidenyl-2-thioxo-4-imidazolidinone (14)

7.3 g of benzaldehyde is added to a mixture of 8 g of 2-thiohydantoin, 40 g of anhydrous sodium acetate and 60 ml of glacial acetic acid. On heating, the mixture slowly becomes liquid and this solution is refluxed gently for 2 hours, allowed to cool for a few minutes, and then poured onto ice/water. The yellow-brown precipitate is filtered off and washed thoroughly with water before drying to yield 12.7 g of the title compound. Recrystallization from ethanol/water gives a pure sample melting at 258° C.

The 2-thioxo-4-imidazolidinones 15 to 24 (Table II) are prepared pared by using an equivalent amount of the appropriate aldehyde or ketone in place of the benzaldehyde used in the above procedure.

TABLE II $$\begin{array}{c} O \\ \parallel \\ HN-C-A \\ | \quad | \\ C-NH \\ \parallel \\ S \end{array}$$

$$A = -C=C\begin{matrix} R^3 \\ \diagup \\ \diagdown R^4 \end{matrix}$$

| | R³ | R⁴ | m.p. (°C.) | nmr ($\delta_{TMS} = 0$)[1] | |
|---|---|---|---|---|---|
| 14. | H | —C₆H₅ (phenyl) | 258° | δ = 6.47<br>7.50 | (singlet, 1H)<br>(multiplet, 5H) |
| 15. | H | CH₃O—C₆H₄— | 260° | δ = 3.80<br>6.40<br>7.30 | (singlet, 3H)<br>(singlet, 1H)<br>(quartet, 4H) |
| 16. | H | NO₂—C₆H₄— | >275° | δ = 6.50<br>8.10 | (singlet, 1H)<br>(quartet, 4H) |
| 17. | H | CF₃—C₆H₄— | 172° | δ = 6.50<br>7.80 | (singlet, 1H)<br>(quartet, 4H) |
| 18. | H | C₆H₅—CH=CH— | 262–3° | δ = 6.03<br>6.75–7.8 | (singlet, 1H)<br>(multiplet, 7H) |
| 19. | H | 2-furyl— | | δ = 6.40<br>6.63<br>7.12<br>7.80 | (singlet, 1H)<br>(quartet, 1H)<br>(doublet, 1H)<br>(doublet, 1H) |
| 20. | H | 2-furyl-CH=CH— | | δ = 6.12<br>6.48<br>6.85<br>6.90<br>7.60 | (doublet, 1H)<br>(multiplet, 2H)<br>(quartet, 1H)<br>(doublet, 1H)<br>(doublet, 1H) |
| 21.[2] | H | CH₃— | 253–5° | δ = 1.85<br>5.67 | (doublet, 3H)<br>(quartet, 1H) |
| 22. | H | CH₃(CH₂)₂— | — | δ = 0.90<br>1.37<br>2.27<br>5.61 | (triplet, 3H)<br>(multiplet, 2H)<br>(quartet, 2H)<br>(triplet, 1H) |
| 23. | H | CH₃(CH₂)₄ | — | δ = 1.18<br>2.24<br>5.40 | (multiplet, 9H)<br>(quartet, 2H)<br>(triplet, 1H) |
| 24. | —(CH₂)₅— | | 150–2° | δ = 1.57<br>2.37<br>2.80 | (broad, 6H)<br>(broad, 2H)<br>(broad, 2H) |

Footnotes:
[1] All compounds dissolved in DMSO-d₆ for nmr measurement.
[2] Acetaldehyde diethylacetal used in place of the lower boiling acetaldehyde.

EXAMPLE C

5-(3-Pyridylidenyl)-2-thioxo-4-imidazolidinone (25)

2.64 g of 3-pyridine carboxaldehyde, 4.0 g of 1-acetyl-2-thiohydantoin, and 2.12 g of anhydrous sodium acetate are added to 20 ml of acetic anhydride and the mixture heated to 116° for 35 minutes. The resulting slurry is filtered and the solid washed thoroughly with hot water, then dried to yield 3.8 g of the title compound.

nmr in DMSO-d₆: δ=6.36 (singlet, 1H), 7.25 (multiplet, 2H), 7.8–8.7 (multiplet, 2H).

EXAMPLE D 5-(2-Propylidenyl)-2-thioxo-4-imidazolidinone (26)

5.8 g of acetone is added dropwise to a well stirred solution of 5.8 g of 2-thiohydantoin in 12.5 ml of pyridine and 2.5 ml of piperidine. The reaction is left to stir for 15 hours at room temperature, and the product which precipitated during this time is filtered off to yield 6.6 g of the title compound which is recrystallized from ethanol.

TLC: silica gel; Ethylacetate/hexane (3:2) $R_f$=0.6.

nmr in DMSO-d$_6$=δ=1.43 (singlet, 3H), 2.45 (singlet, 3H).

EXAMPLE E 5-(2-Methylbutylidenyl)-2-thioxo-4-imidazolidinone (28)

4.0 ml of piperidine is added to a mixture of 4.6 g of 2-thiohydantoin and 3.78 g of 2-methylbutyraldehyde in 60 ml of anhydrous ethanol. The mixture is refluxed for 15 minutes and then the solvent evaporated in vacuo. The residue is suspended in a small volume of water and the resulting solid filtered off, washed with water, and dried to yield 4.1 g (56%) of the title compound.

m.p. 120°-2° C.

TLC: silica gel; Ethylacetate $R_f$=0.7.

nmr in DMSO-d$_6$ δ=0.60-1.77 (multiplet, H), 5.23 (doublet, 1H).

The 2-thioxo-4-imidazolidinones 27 and 29 to 31 (Table III) are prepared by using an equivalent amount of the appropriate aldehyde in place of the 2-methylbutyraldehyde used in the above procedure.

TABLE III

| R$^3$ | R$^4$ | m.p. (°C.) | nmr$^{(1)}$(δ$_{TMS}$ = 0) |
|---|---|---|---|
| 27. H | CH$_3$—CH—<br>\|<br>CH$_3$ | — | δ = 1.00 (doublet, 6H)<br>2.90 (multiplet, 1H)<br>5.40 (doublet, 1H) |
| 28. H | CH$_3$CH$_2$CH—<br>\|<br>CH$_3$ | 120-2° | δ = 0.60–1.77 (multiplet, 8H)<br>2.56 (multiplet, 1H)<br>5.23 (doublet, 1H) |
| 29. H | CH$_3$(CH$_2$)$_3$— | — | δ = 0.53–1.80 (multiplet, 9H)<br>5.45 (triplet, 1H) |
| 30. H | (phenyl)-O-(phenyl)- | 190° | δ = 6.50 (singlet, 1H)<br>7.30 (multiplet, 9H) |
| 31. H | (phenyl)-O-(phenyl)- (meta) | 180° | δ = 6.30 (singlet, 1H)<br>7.00 (multiplet, 9H) |

EXAMPLE F 5-(3-Phenoxybenzylidenyl)-2-methylthio-4-imidazolidinone (61)

0.79 g of iodomethane is added to a stirred suspension of 1.5 g of 5-(3-phenoxybenzylidenyl)-2-thioxo-4-imidazolidinone and 0.77 g of anhydrous potassium carbonate in 50 mls of dry acetonitrile. The mixture is stirred vigorously for 2 hours at room temperature, then filtered, and the filtrate evaporated to dryness. The residue is crystallized from aqueous methanol to yield 1.1 g of the title compound. m.p. 160° C.

TLC: silica gel; ethyl acetate $R_f$=0.45.

nmr in DMSO-d$_6$ δ=2.45 (singlet, 3H), 6.60 (singlet, 1H), 7.30 (multiplet, 8H), 8.00 (singlet, 1H).

The 2-methylthioimidazolidinones 32 to 60 (Table IV) are prepared by using the appropriate 2-thioxo compounds from examples A, B, D and E in place of the 3-phenoxybenzylidenyl imidazolidinone used in the above procedure. When not easily crystallized from the reaction mixture, the methylthio compounds are purified by column chromatography on silica gel, eluting with ethyl acetate or chloroform/methanol.

TABLE IV

| R$^1$ | R$^2$ | nmr$^1$ (δ$_{TMS}$ = 0) |
|---|---|---|

TABLE IV-continued

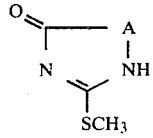

| | | | nmr[1] ($\delta_{TMS} = 0$) |
|---|---|---|---|
| 32. | H | H | $\delta =$ 2.50 (singlet 3H), 3.98 (singlet 2H) |
| 33. | H | CH$_3$— | $\delta$ 1.23 (doublet, 3H), 2.50 (singlet, 3H), 3.97 (quartet, 1H) |
| 34. | H | CH$_3$CH$_2$— | $\delta =$ 0.83 (triplet, 3H), 1.66 (multiplet, 2H), 2.47 (singlet, 3H), 3.87 (triplet, 1H) |
| 35. | H | CH$_3$(CH$_2$)$_2$— | $\delta =$ 0.63–1.80 (multiplet, 7H) 2.47 (singlet, 3H), 3.93 (triplet, 1H) |
| 36. | H | (CH$_3$)$_2$CH— | $\delta$ 0.80 (doublet, 3H), 1.00 (doublet, 3H), 2.53 (singlet, 3H), 3.90 (doublet, 1H) |
| 37. | H | CH$_3$(CH$_2$)$_3$— | $\delta =$ 1.27 (multiplet, 9H), 2.50 (singlet, 3H), 3.93 (triplet, 1H) |
| 38. | H | CH$_3$CH$_2$CH(CH$_3$)— | $\delta =$ 0.89–2.04 (multiplet, 3H), 0.85 (triplet, 3H), 0.92 (doublet, 3H), 2.48 (singlet, 3H), 4.05 (triplet, 1H) |
| 39. | H | (CH$_3$)$_2$CHCH$_2$— | $\delta =$ 0.93 (doublet, 6H), 2.50 (singlet, 3H) 1.30–2.03 (multiplet 3H), 3.97 (multiplet, 1H) |
| 40. | H | CH$_3$(CH$_2$)$_5$— | $\delta =$ 1.30 (multiplet, 13H), 2.53 (singlet, 3H), 4.00 (triplet, 1H) |
| 41. | H | CH$_3$SO$_2$(CH$_2$)$_2$— | $\delta =$ 1.97 (multiplet, 4H), 2.50 (singlet, 3H), 2.97 (singlet, 3H), 4.17 (triplet, 1H) |
| 42. | H | PhCH$_2$— | $\delta =$ 2.48 (singlet, 3H), 2.95 (doublet, 2H) 4.27 (triplet, 1H), 7.17 (singlet, 5H) |
| 43. | H | CH$_3$OCO(CH$_2$)$_2$— | $\delta =$ 1.80–2.80 (multiplet, 4H) 2.50 (singlet, 3H), 3.62 (singlet, 3H), 4.00 (multiplet, 1H) |
| 44. | CH$_3$— | CH$_3$— | $\delta =$ 1.25 (singlet, 6H), 2.47 (singlet, 3H) |
| | R$^3$ | R$^4$ | |
| 45. | H | Ph | $\delta =$ 2.57 (singlet, 3H), 6.67 (singlet, 1H), 7.71 (multiplet, 5H) |
| 46. | H | 4-CH$_3$O-C$_6$H$_4$— | $\delta =$ 2.70 (singlet, 3H), 3.80 (singlet, 3H), 6.80 (singlet, 1H), 7.60 (quartet, 4H) |
| 47. | H | 4-NO$_2$-C$_6$H$_4$— | $\delta =$ 2.90 (singlet, 3H), 6.70 (singlet, 1H), 8.30 (quartet, 4H) |
| 48. | H | 4-CF$_3$-C$_6$H$_4$— | $\delta =$ 2.70 (singlet, 3H), 6.80 (singlet, 1H), 8.00 (quartet, 4H) |

TABLE IV-continued

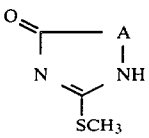

$$A = -\underset{R^2}{\overset{|}{\underset{|}{C}}}-R^1 \qquad A = -\underset{R^4}{\overset{|}{C}}=\underset{}{\overset{R^3}{C}}$$

| | | | nmr$^1$ ($\delta_{TMS} = 0$) |
|---|---|---|---|
| 49. | H | 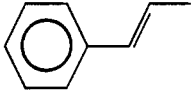 | δ = 2.60 (singlet, 3H),<br>6.53 (doublet, 1H),<br>6.60–7.60 (multiplet, 7H) |
| 50. | H | 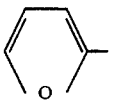 | δ = 2.63 (singlet, 3H),<br>6.52 (singlet, 1H),<br>6.60 (quartet, 1H),<br>7.23 (doublet, 1H),<br>7.75 (doublet, 1H) |
| 51. | H | 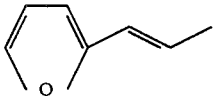 | δ = 2.61 (singlet, 3H),<br>6.52 (multiplet, 4H),<br>6.92 (doublet, 1H),<br>7.60 (doublet, 1H) |
| 52. | H | CH$_3$— | δ = 1.97 (doublet, 3H),<br>2.52 (singlet, 3H),<br>5.93 (quartet, 1H) |
| 53 | H | CH$_3$(CH$_2$)$_2$— | δ = 0.93 (triplet, 3H),<br>1.5 (multiplet, 2H),<br>2.43 (quartet, 2H),<br>2.56 (singlet, 3H),<br>6.05 (triplet, 1H) |
| 54. | H | CH$_3$(CH$_2$)$_4$— | δ = 1.18 (multiplet, 9H),<br>2.55 (singlet, 3H),<br>2.38 (quartet, 2H),<br>5.98 (triplet, 1H) |
| 55. | —(CH$_2$)$_5$— | | δ = 1.60 (broad, 6H),<br>2.52 (singlet, 3H),<br>2.60 (broad, 2H),<br>2.94 (broad, 2H) |
| 56. | CH$_3$— | CH$_3$— | δ = 2.10 (singlet, 3H),<br>2.20 (singlet, 3H),<br>2.50 (singlet, 3H) |
| 57. | H | CH$_3$—CH—<br>       \|<br>      CH$_3$ | δ = 1.07 (doublet, 6H),<br>2.60 (singlet, 3H),<br>2.50 (multiplet, 1H),<br>5.87 (doublet, 1H) |
| 58. | H | CH$_3$CH$_2$CH—<br>           \|<br>          CH$_3$ | δ = 0.60–1.66 (multiplet, 8H),<br>2.46 (multiplet, 1H),<br>2.57 (singlet, 3H),<br>5.80 (doublet, 1H) |
| 59. | H | CH$_3$(CH$_2$)$_3$— | δ = 0.51–1.78 (multiplet, 9H),<br>2.56 (singlet, 3H),<br>5.93 (triplet, 1H) |
| 60. | H | 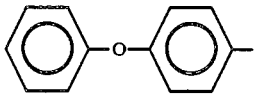 | δ = 2.7 (singlet, 3H),<br>6.7 (singlet, 1H),<br>7.2 (multiplet, 9H) |

TABLE IV-continued

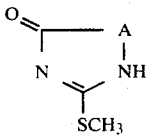

| | nmr¹ ($\delta_{TMS} = 0$) |
|---|---|
| 61. H 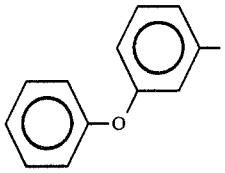 | $\delta =$ 2.5 (singlet, 3H), 6.6 (singlet, 1H), 7.3 (multiplet, 8H), 8.0 (singlet, 1H) |

EXAMPLE G 5-(3-Pyridylidenyl)-2-methylthio-4-imidazolidinone (62)

4.10 g of 5-(3-pyridylidenyl)-2-thioxo-4-imidazolidinone is dissolved in 200 ml of 0.5N potassium hydroxide to form a green solution. 5.04 g of dimethylsulphate is added dropwise to the stirred solution at room temperature. After stirring for 1 hour, the precipitate which has formed is filtered off, washed with cold water, and dried to yield 2.01 g (46%) of title compound.

NMR in DMSO-$d_6$=2.63 (singlet, 3H), 6.57 (singlet, 1H), 7.26 (multiplet, 1H), 8.37 (multiplet, 2H), 9.00 (broad singlet, 1H).

EXAMPLE H 5,5-Diphenyl-2-methylthio-4-imidazolidinone (63)

7.0 g of 5,5-diphenyl-2-thiohydantoin is dissolved in 50 ml of ethanol and 10 ml of 3N sodium carbonate added followed by 3 ml of iodomethane. The mixture is refluxed for 18 hours, then cooled and the solvent evaporated. The residual solid is recrystallized from ethanol to give 4.6 g (60%) of the title compound.

TLC: silica gel: CHCl$_3$/MeOH (4:1) $R_f$=0.71.

nmr in DMSO-$d_6$ $\delta$=2.63 (singlet, 3H), 7.27 (singlet, 10H).

EXAMPLE I

2[2-[(2-Guanidino-4-thiazolyl)]methylthio]ethylamino-5-(3-phenoxybenzylidenyl)-imidazolidin-4-one (96)

0.4 g of 2-guanidino-4-[(2-aminoethyl)thiomethyl]-thiazole dihydrochloride is thoroughly mixed with a solution of 0.15 g (2.6 mmoles) of potassium hydroxide in 15 ml of absolute ethanol. The precipitated potassium chloride is filtered off and washed with 5 ml of absolute ethanol. To this filtrate is added 0.5 g of 2-methylthio-5-(3-phenoxybenzylidenyl)-imidazolidin-4-one and the solution refluxed until TLC indicates the disappearance of starting thiazole (approximately 6 hours). The solvent is then evaporated to dryness and the product purified by column chromatography on silica gel, eluting with a mixture of 85% chloroform, 14% methanol, 1% concentrated aqueous ammonia. 223 mg of the title compound is obtained.

TLC: silica gel, CHCl$_3$/CH$_3$OH/NH$_4$OH (70:25:1) $R_f$=0.56.

nmr in DMSO-$d_6$ $\delta$=2.66 (triplet 2H), 3.44 (multiplet 2H), 3.64 (singlet 2H), 6.28 (singlet 1H), 6.48 (singlet 1H), 7.10 (multiplet 8H), 7.80 (broad singlet 1H).

The 2-guanidino-4-thiazolylmethylthioethyl-imidazolidinones 64 to 97 (Table V) are prepared according to the above procedure by substituting the appropriate 2-methylthio compounds from examples F, G and H.

TABLE V

[Structure: thiazole ring with S-CH2 attached, connected via CH2-S-CH2CH2-NH-C(=N-A-H)-N=... amidine substructure, with NH2-C(=N)-NH2 group on thiazole]

A = −C(R¹)(R²)−    or    A = −C(R³)=C(R⁴)−... (alkene form on right)

| | R¹ | R² | NMR$^{(1)}$ ($\delta_{TMS} = 0$) |
|---|---|---|---|
| 64. | H | H | δ = 2.62 (triplet 2H), 3.42 (multiplet 2H), 3.64 (singlet 2H), 3.71 (singlet 2H), 6.70 (singlet 1H) |
| 65. | H | CH$_3$ | δ = 1.22 (doublet 3H), 2.64 (triplet 2H), 3.44 (multiplet 2H), 3.66 (singlet 2H), 3.98 (quartet 1H), 6.43 (singlet 1H) |

| | R¹ | R² | NMR |
|---|---|---|---|
| 66. | H | CH$_3$CH$_2$— | δ = 0.83 (triplet 3H), 1.68 (multiplet 2H), 2.62 (triplet 2H), 3.38 (multiplet 2H), 3.70 (singlet 2H), 3.88 (multiplet 1H), 6.60 (singlet 1H) |
| 67. | H | CH$_3$(CH$_2$)$_2$— | δ = 0.60–1.76 (multiplet 7H), 2.60 (triplet 2H), 3.42 (multiplet 2H), 3.68 (singlet 2H), 3.93 (multiplet 1H), 6.72 (singlet 1H) |
| 68. | H | CH$_3$CH(CH$_3$)— | δ = 0.77 (doublet 3H), 0.93 (doublet 3H), 2.08 (multiplet 1H), 2.63 (triplet 2H), 3.40 (multiplet 2H), 3.58 (singlet 2H), 3.82 (multiplet 1H), 6.60 (singlet 1H) |
| 69. | H | CH$_3$(CH$_2$)$_3$— | δ = 1.15 (multiplet 9H), 2.66 (triplet 2H), 3.42 (multiplet 2H), 3.66 (singlet 2H), 3.70 (multiplet 1H), 6.63 (singlet 1H) |
| 70. | H | CH$_3$CH$_2$CH(CH$_3$)— | δ = 0.50–2.00 (multiplet 9H), 2.60 (triplet 2H), 3.43 (multiplet 2H), 3.53 (singlet 2H), 3.94 (triplet 1H), 6.58 (singlet 1H) |
| 71. | H | CH$_3$CHCH$_2$— / CH$_3$ | δ = 0.90 (doublet 6H), 1.78 (multiplet 3H), 2.63 (triplet 2H), 3.48 (multiplet 2H), 3.67 (singlet 2H), 3.88 (multiplet 1H), 6.60 (singlet 1H) |
| 72. | H | CH$_2$(CH$_2$)$_5$— | δ = 1.30 (multiplet 13H), 2.60 (triplet 2H), 3.50 (multiplet 2H), 3.60 (singlet 2H), 3.84 (multiplet 1H), 6.48 (singlet 1H) |
| 73. | H | CH$_3$SO$_2$(CH$_2$)$_2$— | δ = 2.00 (multiplet 4H), 2.66 (triplet 2H), 2.88 (singlet 3H), 3.44 (multiplet 2H), 3.60 (singlet 2H), 3.83 (multiplet 1H), 6.43 (singlet 1H) |
| 74. | H | C$_6$H$_5$CH$_2$— | δ = 2.62 (triplet 2H), 3.00 (doublet 2H), 3.48 (multiplet 2H), 3.72 (singlet 2H), 4.40 (triplet 1H), 6.83 (singlet 1H), 7.20 (singlet 5H) |
| 75. | H | CH$_3$OCO(CH$_2$)$_2$— | δ = 1.50–2.80 (multiplet 6H), 3.38 (multiplet 2H), 3.56 (singlet 3H), 3.68 (singlet 2H), 6.72 (singlet 1H) |
| 76. | H | CH$_3$NHCO(CH$_2$)$_2$— | δ = 1.80–3.00 (multiplet 6H), 2.68 (singlet 3H), 3.42 (multiplet 2H), 3.64 (singlet 2H), 6.34 (singlet 1H) |

TABLE V-continued

[Structure: thiazole ring with CH2-S-CH2CH2-NH-C(=N)-NH-C(=O)-N(A)-N-H guanidine group, and S-C(NH2)=N- on thiazole]

| A = −C(R¹)(R²)− | | A = −C(R³)=C(R⁴)− | |
|---|---|---|---|

| 77. | [phenyl] | [phenyl] | δ = 2.62 (triplet 2H), 3.42 (multiplet 2H), 3.66 (singlet 2H), 6.63 (singlet 1H) 7.20 (singlet 10H) |
|---|---|---|---|
| 78. | CH₃— | CH₃— | δ = 1.18 (singlet 6H), 2.63 (triplet 2H) 3.40 (multiplet 2H), 3.63 (singlet 2H) 6.50 (singlet 1H) |
| 79.(2) | H | KOCO(CH₂)₂— | = 1.55–2.90 (multiplet 6H), 3.40 (multiplet 2H), 3.60 (singlet 2H), 6.65 (singlet 1H) |

|  | R³ | R⁴ | NMR |
|---|---|---|---|
| 80. | H | [phenyl] | δ = 2.62 (triplet 2H), 3.42 (multiplet 2H) 3.70 (singlet 2H), 6.30 (singlet 1H) 6.60 (singlet 1H), 7.20 (multiplet 5H) |
| 81. | H | CH₃O-[phenyl]- | δ = 2.60 (triplet 2H), 3.42 (multiplet 2H) 3.60 (singlet 2H), 3.70 (singlet 3H) 6.10 (singlet 1H), 6.30 (singlet 1H) 7.20 (quartet 4H) |
| 82. | H | NO₂-[phenyl]- | δ = 2.62 (triplet 2H), 3.40 (multiplet 2H) 3.60 (singlet 2H), 6.30 (singlet 1H) 6.50 (singlet 1H), 8.10 (singlet 4H) |
| 83. | H | CF₃-[phenyl]- | δ = 2.60 (triplet 2H), 3.64 (multiplet 2H) 3.70 (singlet 2H), 6.20 (singlet 1H) 6.40 (singlet 1H), 7.70 (quartet 4H) |
| 84. | H | [phenyl-CH=CH-] | δ = 2.67 (triplet 2H), 3.50 (multiplet 2H) 3.65 (singlet 2H), 6.1 (doublet 1H) 6.50 (singlet 1H), 6.55–7.6 (multiplet 7H) |
| 85. | H | [furyl] | δ = 2.73 (triplet 2H), 3.60 (multiplet 2H) 3.66 (singlet 2H), 6.13 (singlet 1H) 6.47 (singlet 1H), 6.62 (quartet 1H) 7.26 (doublet 1H), 7.80 (doublet 1H) |
| 86. | H | [furyl-CH=CH-] | δ = 2.68 (triplet 2H), 3.50 (multiplet 2H) 3.70 (singlet 1H), 6.06 (doublet 1H) 6.42 (singlet 2H), 6.74 (multiplet 2H) 7.52 (singlet 1H), 7.40 (multiplet 1H) |
| 87. | H | CH₃— | δ = 1.73 (doublet 3H), 2.60 (triplet 2H) 3.42 (multiplet 2H), 3.57 (singlet 2H) 5.33 (quartet 1H), 6.30 (singlet 1H) |
| 88. | H | CH₃(CH₂)₂— | δ = 0.94 (triplet 3H), 1.5–2.5 (multiplet 4H) 2.66 (triplet 2H), 3.58 (multiplet 2H) 3.66 (singlet 2H), 5.60 (triplet 1H) 6.80 (singlet 1H) |
| 89. | H | CH₃(CH₂)₄— | δ = 1.13 (multiplet 9H), 2.10 (quartet 2H) |

TABLE V-continued

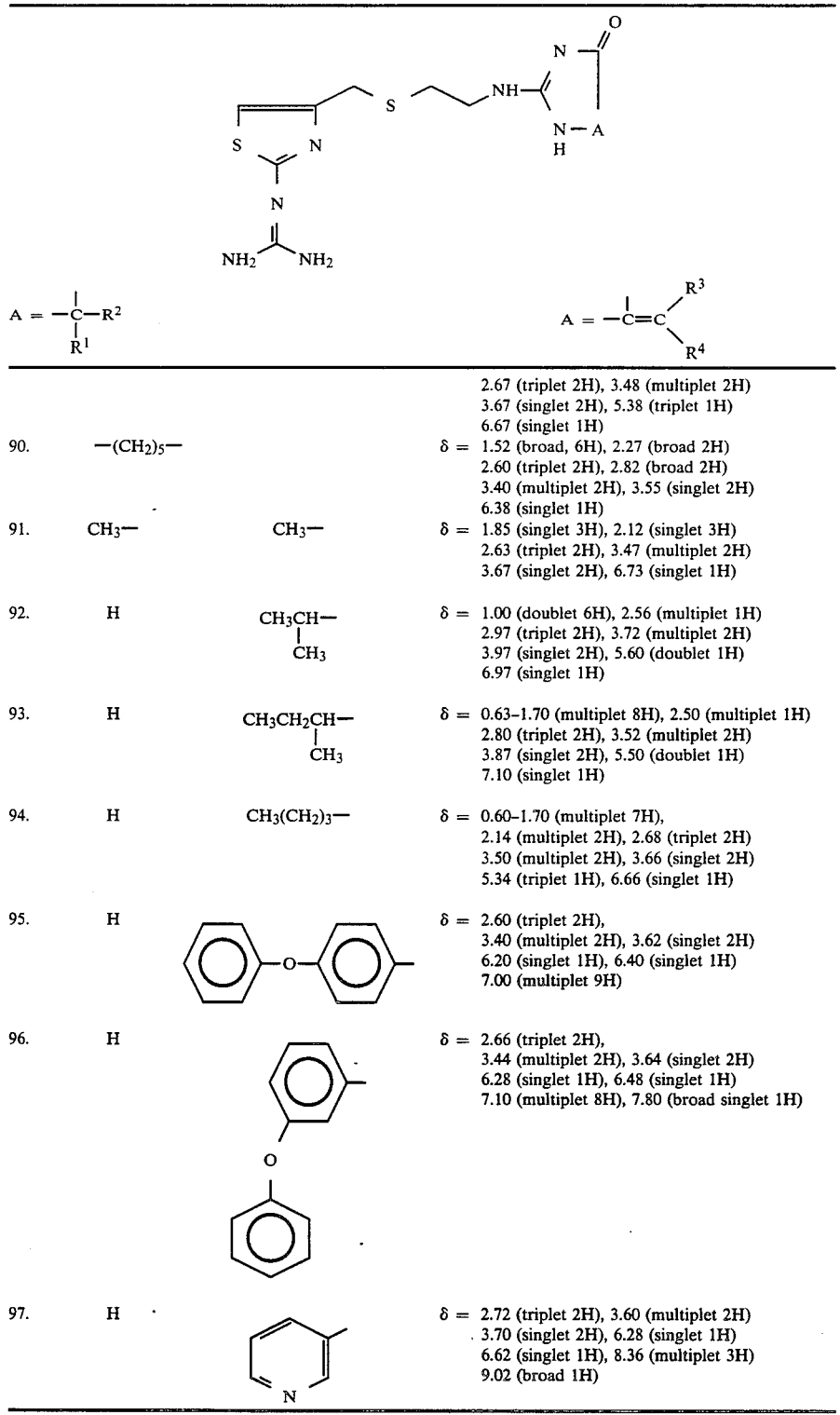

| # | A = $-\underset{R^1}{\overset{R^2}{\underset{|}{\overset{|}{C}}}}-R^2$ | A = $-\underset{}{\overset{R^3}{\underset{R^4}{\overset{|}{C}=C}}}$ | NMR |
|---|---|---|---|
| | | | 2.67 (triplet 2H), 3.48 (multiplet 2H) |
| | | | 3.67 (singlet 2H), 5.38 (triplet 1H) |
| | | | 6.67 (singlet 1H) |
| 90. | —(CH$_2$)$_5$— | | δ = 1.52 (broad, 6H), 2.27 (broad 2H) |
| | | | 2.60 (triplet 2H), 2.82 (broad 2H) |
| | | | 3.40 (multiplet 2H), 3.55 (singlet 2H) |
| | | | 6.38 (singlet 1H) |
| 91. | CH$_3$— | CH$_3$— | δ = 1.85 (singlet 3H), 2.12 (singlet 3H) |
| | | | 2.63 (triplet 2H), 3.47 (multiplet 2H) |
| | | | 3.67 (singlet 2H), 6.73 (singlet 1H) |
| 92. | H | $\underset{CH_3}{\overset{CH_3CH-}{|}}$ | δ = 1.00 (doublet 6H), 2.56 (multiplet 1H) |
| | | | 2.97 (triplet 2H), 3.72 (multiplet 2H) |
| | | | 3.97 (singlet 2H), 5.60 (doublet 1H) |
| | | | 6.97 (singlet 1H) |
| 93. | H | $\underset{CH_3}{\overset{CH_3CH_2CH-}{|}}$ | δ = 0.63–1.70 (multiplet 8H), 2.50 (multiplet 1H) |
| | | | 2.80 (triplet 2H), 3.52 (multiplet 2H) |
| | | | 3.87 (singlet 2H), 5.50 (doublet 1H) |
| | | | 7.10 (singlet 1H) |
| 94. | H | CH$_3$(CH$_2$)$_3$— | δ = 0.60–1.70 (multiplet 7H), |
| | | | 2.14 (multiplet 2H), 2.68 (triplet 2H) |
| | | | 3.50 (multiplet 2H), 3.66 (singlet 2H) |
| | | | 5.34 (triplet 1H), 6.66 (singlet 1H) |
| 95. | H | ⌬—O—⌬— | δ = 2.60 (triplet 2H), |
| | | | 3.40 (multiplet 2H), 3.62 (singlet 2H) |
| | | | 6.20 (singlet 1H), 6.40 (singlet 1H) |
| | | | 7.00 (multiplet 9H) |
| 96. | H | ⌬(—O—⌬)— | δ = 2.66 (triplet 2H), |
| | | | 3.44 (multiplet 2H), 3.64 (singlet 2H) |
| | | | 6.28 (singlet 1H), 6.48 (singlet 1H) |
| | | | 7.10 (multiplet 8H), 7.80 (broad singlet 1H) |
| 97. | H | (pyridyl) | δ = 2.72 (triplet 2H), 3.60 (multiplet 2H) |
| | | | 3.70 (singlet 2H), 6.28 (singlet 1H) |
| | | | 6.62 (singlet 1H), 8.36 (multiplet 3H) |
| | | | 9.02 (broad 1H) |

[1] All samples were dissolved in DMSO-d$_6$ for NMR measurements.
[2] Prepared by hydrolysis of the ester 75 in KOH/methanol.

What is claimed is:
1. A compound of the formula I

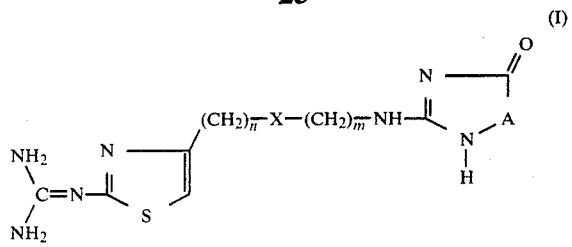

(I)

in which
X represents —O—, —CH₂—, —S—, or —NH—,
n represents 1 or 2,
m represents 2, 3 or 4, and
A represents

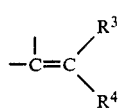

in which
R³ and R⁴, which may be the same or different, each represents
a hydrogen atom;
a straight or branched chain alkyl group having from 1 to 10 carbon atoms or
an alkenyl group having from 2 to 10 carbon atoms, wherein said alkyl or alkenyl group is unsubstituted or substituted by one or more groups, which may be the same or different, selected from the group consisting of hydroxyl groups; —OR⁶ groups in which R⁶ represents a lower alkyl group or a phenyl group; —NR⁷R⁸ groups in which R⁷ and R⁸ each denotes a hydrogen atom, a lower alkyl group, a phenyl group, or a lower acyl group; —COOR⁹ groups, in which R⁹ represents a hydrogen atom or a lower alkyl group; —CONR⁷R⁸ in which R⁷ and R⁸ are as defined above and in addition together with the N atom may form a 5 or 6 membered ring; phenyl groups which are unsubstituted or substituted by a lower alkyl, lower alkoxy, phenoxy, halogen, dimethylaminomethyl, trifluoromethyl, nitro, cyano, sulphonic acid or sulphonamide substituent; heterocyclic groups selected from the group consisting of pyridine, thiophen and furan groups, which are unsubstituted or substituted as defined above for said phenyl groups, lower alkylsulphonyl and phenylsulphonyl groups, and nitrile groups;

a phenyl group or a phenyl group bearing one or more substituents selected from the group consisting of (C₁-C₄) lower alkyl, (C₁-C₄) lower alkoxy, phenoxy, chlorine, bromine, iodine, fluorine, dimethylaminomethyl, trifluoromethyl, nitro, cyano, sulphonic acid and sulphonamide substituents; or a five or six membered heterocycle selected from the group consisting of pyridine, thiophen, furan and tetrahydrofuran; or R³ and R⁴ together with the carbon atom to which they are bonded form a cyclohexyl or cyclopentyl ring;

or a physiologically tolerable salt thereof.

2. A compound of Formula I as claimed in claim 1 wherein
A represents

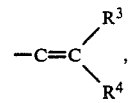

R³ being hydrogen and
R⁴ being straight or branched chain alkyl having from 1 to 6 carbon atoms.

3. A compound of the formula I as claimed in claim 1, wherein said alkyl or alkenyl group has up to 6 carbon atoms.

4. A physiologically tolerable salt of a compound of the formula I as claimed in claim 1.

5. A pharmaceutical preparation which comprises, as active ingredient, a compound of the formula I as claimed in claim 1 or a physiologically tolerable salt thereof, in admixture or conjunction with a pharmaceutically suitable carrier.

6. A pharmaceutical preparation as claimed in claim 5, containing from 0.01 to 10 mg of the active ingredient per kg body weight.

7. Method for the treatment of pathological conditions resulting from hypersecretion of gastric acid by administering to the patient an effective amount of a compound of formula I as claimed in claim 1.

* * * * *